US010399952B2

(12) United States Patent
Wöll et al.

(10) Patent No.: US 10,399,952 B2
(45) Date of Patent: Sep. 3, 2019

(54) PROCESS FOR THE EPOXIDATION OF PROPENE

(71) Applicants: EVONIK DEGUSSA GMBH, Essen (DE); THYSSENKRUPP INDUSTRIAL SOLUTIONS AG, Essen (DE)

(72) Inventors: Wolfgang Wöll, Maintal (DE); Marc Brendel, Bruchköbel (DE); Bernd Jaeger, Bickenbach (DE); Niels Bredemeyer, Waltrop (DE); Bärbel Kolbe, Witten (DE); Norbert Ullrich, Essen (DE); Maik Bernhard, Frankfurt (DE)

(73) Assignees: Evonik Degussa GmbH, Essen (DE); thyssenkrupp Industrial Solutions AG, Essen (DE)

( * ) Notice: Subject to any disclaimer, the term of this patent is extended or adjusted under 35 U.S.C. 154(b) by 0 days.

(21) Appl. No.: 16/086,309

(22) PCT Filed: Mar. 10, 2017

(86) PCT No.: PCT/EP2017/055656
§ 371 (c)(1),
(2) Date: Sep. 18, 2018

(87) PCT Pub. No.: WO2017/162446
PCT Pub. Date: Sep. 28, 2017

(65) Prior Publication Data
US 2019/0100501 A1 Apr. 4, 2019

(30) Foreign Application Priority Data
Mar. 21, 2016 (EP) .................................... 16161439

(51) Int. Cl.
*B01J 8/02* (2006.01)
*B01J 8/06* (2006.01)
*C07D 301/12* (2006.01)
*C07D 301/32* (2006.01)
*C07D 301/36* (2006.01)
*C07D 303/04* (2006.01)

(52) U.S. Cl.
CPC .......... *C07D 301/12* (2013.01); *B01J 8/0257* (2013.01); *B01J 8/067* (2013.01); *C07D 303/04* (2013.01); *B01J 2208/00212* (2013.01); *B01J 2208/00548* (2013.01); *B01J 2208/065* (2013.01); *C07D 301/32* (2013.01); *C07D 301/36* (2013.01)

(58) Field of Classification Search
CPC .... C07D 301/12; C07D 303/04; B01J 8/0257; B01J 8/067
USPC ....................................................... 549/531
See application file for complete search history.

(56) References Cited

U.S. PATENT DOCUMENTS

| 4,308,409 | A | 12/1981 | Wu et al. |
| 5,274,140 | A | 12/1993 | Venturello et al. |
| 5,591,875 | A | 1/1997 | Chang et al. |
| 5,599,956 | A | 2/1997 | Pujado et al. |
| 6,372,924 | B2 | 4/2002 | Thiele |
| 6,673,950 | B1 | 1/2004 | Teles et al. |
| 6,861,042 | B2 | 3/2005 | Korl et al. |
| 7,169,945 | B2 | 1/2007 | Haas et al. |
| 7,173,143 | B2 | 2/2007 | Bender et al. |
| 7,601,263 | B2 | 10/2009 | Ebert et al. |
| 7,658,893 | B2 | 2/2010 | Bassler et al. |
| 7,670,572 | B2 | 3/2010 | Porscha et al. |
| 7,833,498 | B2 | 11/2010 | Goebbel et al. |
| 7,863,211 | B2 | 1/2011 | Strebelle et al. |
| 8,545,673 | B2 | 10/2013 | Dietz et al. |
| 9,539,549 | B2 | 1/2017 | Haensel et al. |
| 10,053,438 | B2 | 8/2018 | Bolz et al. |
| 10,053,440 | B2 | 8/2018 | Bolz et al. |
| 10,087,158 | B2 | 10/2018 | Stock et al. |
| 10,100,024 | B2 | 10/2018 | Stochniol et al. |

(Continued)

FOREIGN PATENT DOCUMENTS

| DE | 195 07 584 | 9/1996 |
| EP | 0 100 119 | 2/1984 |

(Continued)

OTHER PUBLICATIONS

Shin; Ind. Eng. Chem. Res. 2010, 49, 8125-8134. (Year: 2010).*
Wang; Asian Journal of Chemistry; vol. 26, No. 4 (2014), 943-950. (Year: 2014).*
International Search Report for PCT/EP2017/055656 filed Mar. 10, 2017.
Written Opinion of the International Searching Authority for PCT/EP2017/055656 filed Mar. 10, 2017.
International Preliminary Report on Patentability for PCT/EP2017/055656 filed Mar. 10, 2017.
PCT Direct Letter sent to the International Bureau for corresponding international application PCT/EP2017/055656 filed Mar. 10, 2017.

(Continued)

*Primary Examiner* — Daniel R Carcanague
(74) *Attorney, Agent, or Firm* — Law Office of: Michael A. Sanzo, LLC

(57) ABSTRACT

During start-up of a continuous epoxidation of propene with hydrogen peroxide in a methanol solvent with a shaped titanium silicalite catalyst in a tube bundle reactor with a cooling jacket, cooling medium is fed at the rate for full load of the reactor with a constant entry temperature of from 20° C. to 50° C., methanol solvent is fed at a rate of from 50 to 100% for full load of the reactor, hydrogen peroxide is fed at a rate that starts with no more than 10% of the rate for full load and is increased continuously or stepwise to maintain a maximum temperature in the fixed bed of no more than 60° C. and a difference between the maximum temperature in the fixed bed and the cooling medium entry temperature of no more than 20° C., and propene is fed at a rate of from 20 to 100% of the rate for full load, increasing the feeding rate when the molar ratio of propene to hydrogen peroxide reaches the molar ratio for full load.

20 Claims, No Drawings

(56) References Cited

U.S. PATENT DOCUMENTS

| | | |
|---|---|---|
| 10,125,108 B2 | 11/2018 | Jahn et al. |
| 10,214,471 B2 | 2/2019 | Wiederhold et al. |
| 10,214,504 B2 | 2/2019 | Brendel et al. |
| 2003/0040637 A1 | 2/2003 | Hofen et al. |
| 2005/0245751 A1 | 11/2005 | Bender et al. |
| 2006/0014970 A1 | 1/2006 | Goebbel et al. |
| 2006/0058539 A1 | 3/2006 | Babler et al. |
| 2007/0004926 A1 | 1/2007 | Schindler et al. |
| 2012/0142950 A1 | 6/2012 | Teles et al. |
| 2015/0007951 A1 | 1/2015 | Dietz et al. |
| 2017/0210718 A1 | 7/2017 | Stochinol et al. |
| 2018/0002299 A1 | 1/2018 | Bolz et al. |
| 2018/0002300 A1 | 1/2018 | Bolz et al. |
| 2018/0030010 A1 | 2/2018 | Breitenbach et al. |
| 2018/0030011 A1 | 2/2018 | Stock et al. |
| 2018/0030012 A1 | 2/2018 | Stock et al. |
| 2018/0057473 A1 | 3/2018 | Stock et al. |
| 2018/0134676 A1 | 5/2018 | Jahn et al. |
| 2018/0346432 A1 | 12/2018 | Hofen et al. |
| 2018/0354878 A1 | 12/2018 | Wiederhold et al. |
| 2018/0354923 A1 | 12/2018 | Pascaly et al. |
| 2018/0370934 A1 | 12/2018 | Brendel et al. |
| 2019/0023673 A1 | 1/2019 | Schmidt et al. |

FOREIGN PATENT DOCUMENTS

| | | |
|---|---|---|
| EP | 0 230 949 | 8/1987 |
| EP | 0 659 473 | 6/1995 |
| EP | 0 757 045 | 2/1997 |
| EP | 1 247 806 | 10/2002 |
| EP | 1 489 074 | 12/2004 |
| WO | WO 02/085873 | 10/2002 |
| WO | WO 03/016296 | 2/2003 |
| WO | WO 03/018567 | 3/2003 |
| WO | WO 03/093255 | 11/2003 |
| WO | WO 2004/018088 | 3/2004 |
| WO | WO 2004/028962 | 4/2004 |
| WO | WO 2004/048335 | 6/2004 |
| WO | WO 2004/048354 | 6/2004 |
| WO | WO 2004/048355 | 6/2004 |
| WO | WO 2005/000827 | 1/2005 |
| WO | WO 2005/103024 | 11/2005 |
| WO | WO 2008/141734 | 11/2008 |
| WO | WO 2011/063937 | 6/2011 |
| WO | WO 2016/016070 | 2/2016 |

OTHER PUBLICATIONS

Chowdhury, et al, "Recovery of Homogeneous Polyoxometallate Catalysts from Aqueous and Organic Media by a Mesoporous Ceramic Membrane without Loss of Catalytic Activity," *Chem. Eur. J.* 12(11):3061-3066 (Apr. 2006).

Guojie, et al., "Factors Affecting Propylene Epoxidation Catalyzed by Reaction-Controlled Phase-Transfer Catalyst," *Chinese Journal of Catalysis* 26:1005-1010 (Nov. 2005), with English language abstract on p. 1 of the article.

Kaur, et al., "Poloxometalate-catalysed epoxidation of propylene with hydrogen peroxide: microemulsion versus biphasic process," *Catalysis Communications* 5(11): 709-713 (Nov. 2004).

Li, et al., "Influence of composition of heteropolyphophatotungstate catalyst on epoxidation of propylene," *Journal of Molecular Catalysis A: Chemical* 218(2):247-252 (Aug. 2004).

Luthra, et al., "Homogeneous phase transfer catalyst recovery and re-use using solvent resistant membranes," *Journal of Membrane Science* 201:65-75 (2002).

Venturello, et al., "A New, Effective Catalytic System for Epoxidation of Olefins by Hydrogen Peroxide under Phase-Transfer Conditions," *J. Org. Chem.* 483831-3833 (1983).

Ullmann Encylopedia of Industrial Chemistry, online edition 2013, entry "propene," DOI 10.1002/14356007.a22_211.pub3.

U.S. Appl. No. 15/778,318, filed Nov. 1, 2016, US-2018/0370934 A1, Dec. 27, 2018, Brendel.

U.S. Appl. No. 15/778,337, filed May 23, 2018, US-2018/0354923 A1, Dec. 13, 2018, Pascaly.

U.S. Appl. No. 15/778,425, filed May 23, 2018, US-2018/0346432 A1, Dec. 6, 2018, Hofen.

U.S. Appl. No. 15/778,562, filed May 23, 2018, US-2018/0354878 A1, Dec. 13, 2018, Wiederhold.

U.S. Appl. No. 16/070,873, filed Jul. 18, 2018, Schmidt.

U.S. Appl. No. 16/302,099, filed Nov. 15, 2018, Wiederhold.

\* cited by examiner

PROCESS FOR THE EPOXIDATION OF PROPENE

CROSS REFERENCE TO RELATED APPLICATIONS

The present application is US national stage of international application PCT/EP2017/055656, which had an international filing date of Mar. 10, 2017, and which was published in English on Sep. 28, 2017. Priority is claimed to European application EP 16161439.1, filed on Mar. 21, 2016.

FIELD OF THE INVENTION

The present invention relates to a process for the epoxidation of propene with hydrogen peroxide in the presence of a titanium silicalite fixed bed catalyst.

BACKGROUND OF THE INVENTION

The liquid phase epoxidation of propene with hydrogen peroxide in the presence of a titanium silicalite catalyst is known from EP 0 100 119 A1. The reaction is usually carried out with a fixed bed catalyst at a pressure of more than 10 bar to achieve high propene concentrations in the liquid phase reaction mixture. The epoxidation is highly exothermal and requires adequate temperature control, because excessive reaction temperatures lead to increased by-product formation which reduces product selectivity for propene oxide.

EP 1 247 806 A1 describes epoxidation of propene with a titanium silicalite catalyst in a cooled fixed bed reactor using a cooling medium having a minimum temperature of 40° C. and limiting the maximum temperature of the catalyst fixed bed to 60° C. Tubular or multi-tubular reactors having a cooling jacket are used for this purpose.

WO 2005/068062 describes epoxidation of propene with a titanium silicalite catalyst in a tube bundle reactor which has a multitude of parallel reaction tubes cooled with a common cooling jacket. The catalyst is arranged in the tubes and cooling medium is passed through the jacket space in co-current.

SUMMARY OF THE INVENTION

It has now been found that the high catalytic activity of a fresh or regenerated titanium silicalite fixed bed catalyst can lead to breaking of the catalyst shaped bodies during start-up of the epoxidation reaction. It has further been found that a high production rate for propene oxide can be reached in a short time period without such breaking of catalyst shaped bodies when the epoxidation reactor is operated during start-up with full cooling, at least 50% solvent feed and at least 20% propene feed, and the feed rate for hydrogen peroxide is increased at a rate maintaining the maximum temperature in the fixed bed as well as the difference between the maximum temperature in the fixed bed and the cooling medium entry temperature below certain limits.

Subject of the invention is therefore a process for the epoxidation of propene by continuously reacting propene with hydrogen peroxide in a methanol solvent and in the presence of a shaped titanium silicalite catalyst in a tube bundle reactor comprising a multitude of parallel reaction tubes and a cooling jacket enclosing the reaction tubes with the catalyst arranged as a fixed bed in the reaction tubes, the molar ratio of propene to hydrogen peroxide being in the range of from 2.5:1 to 6:1 at full load of the reactor, wherein during start-up of the reaction with a fresh or a regenerated catalyst until full load of the reactor is reached:

cooling medium is fed to the cooling jacket at a constant rate for full load of the reactor, the entry temperature of the cooling medium being kept essentially constant at a value in the range of from 20° C. to 50° C.;

methanol solvent is fed to the reaction tubes at a feeding rate of from 50 to 100% of a feeding rate for full load of the reactor;

hydrogen peroxide is fed to the reaction tubes at a feeding rate that starts with no more than 10% of a feeding rate for full load of the reactor and is increased continuously or stepwise to the rate for full load of the reactor, increasing the feeding rate for hydrogen peroxide to maintain a maximum temperature in the fixed bed of no more than 60° C. and a temperature difference between the maximum temperature in the fixed bed and the cooling medium entry temperature of no more than 20° C.; and propene is fed to the reaction tubes at a feeding rate of from 20 to 100% of a feeding rate for full load of the reactor, increasing the feeding rate for propene when the molar ratio of propene to hydrogen peroxide reaches the molar ratio for full load of the reactor.

DETAILED DESCRIPTION OF THE INVENTION

In the process of the invention, propene is continuously reacted with hydrogen peroxide in a methanol solvent and in the presence of a shaped titanium silicalite catalyst in a tube bundle reactor comprising a multitude of parallel reaction tubes and a cooling jacket enclosing the reaction tubes with the catalyst arranged as a fixed bed in the reaction tubes. The process of the invention comprises a start-up of the reaction with a fresh or a regenerated catalyst followed by carrying out the reaction at full load of the reactor. The term full load of the reactor refers to operation of the reactor at a maximum feed rate for hydrogen peroxide.

The propene may contain propane, preferably with a molar ratio of propane to propene of from 0.001 to 0.15 and more preferably of from 0.08 to 0.12. Hydrogen peroxide can be used as an aqueous solution, preferably containing from 30 to 75% by weight hydrogen peroxide and most preferably from 40 to 70% by weight. The methanol solvent can be a technical grade methanol, a solvent stream recovered in the work-up of the epoxidation reaction mixture or a mixture of both. The methanol solvent is preferably used in a weight ratio of 0.5 to 20 relative to the amount of aqueous hydrogen peroxide solution.

Propene is used in excess to hydrogen peroxide and at full load of the reactor the molar ratio of propene to hydrogen peroxide is in the range of from 2.5:1 to 6:1, preferably from 3:1 to 5:1.

The process of the invention is carried out in a tube bundle reactor which comprises a multitude of parallel reaction tubes and a cooling jacket enclosing the reaction tubes. The tube bundle reactor preferably comprises from 5000 to 20000 parallel reaction tubes, more preferably from 7500 to 15000 parallel reaction tubes. The reaction tubes preferably have a circular cross section with an internal diameter of preferably from 2 to 5 cm, more preferably from 2.5 to 4 cm. Preferably all reaction tubes of the tube bundle reactor have the same internal diameter. The reaction tubes preferably have a length of from 5 to 18 m, more preferably from 10 to 15 m.

The parallel reaction tubes are enclosed by a cooling jacket which preferably has a feed point for cooling medium near the entry of the reaction tubes and a withdrawal point for cooling medium near the end of the reaction tubes. The feed point for cooling medium is preferably less than 1 m downstream from the entry of the reaction tubes and may be as close to the entry of the reaction tubes as technically possible. It may comprise several openings where cooling medium enters the cooling jacket within this distance from the entry of the reaction tubes. The withdrawal point for cooling medium is preferably less than 1 m upstream from the end of the reaction tubes and may be as close to the end of the reaction tubes as technically possible. It may comprise several openings where cooling medium is withdrawn from the cooling jacket within this distance from the end of the reaction tubes. The cooling jacket preferably comprises tube sheets at the entry of the reaction tubes and at the end of the reaction tubes, separating a reactor entry space connected to the entry of all parallel reaction tubes from the cooling jacket and separating a reactor exit space connected to the end of all parallel reaction tubes from the cooling jacket. The cooling jacket may also have one or more additional withdrawal points for cooling medium upstream of the withdrawal point for cooling medium near the end of the reaction tubes. The tube bundle reactor preferably has from 1 to 3 additional withdrawal points for cooling medium, more preferably 1 or 2 additional withdrawal points for cooling medium and most preferably a single additional withdrawal point for cooling medium. The additional withdrawal points are preferably located at from 15 to 70% of the length of the reaction tubes, more preferably at from 18 to 50% of the length, the length being measured from the entry of the reaction tubes to the end of the reaction tubes. When the tube bundle reactor has several additional withdrawal points for cooling medium, they are preferably located at different lengths along the reaction tubes.

The tube bundle reactor preferably comprises a secondary cooling circuit with at least one circulating pump and at least one heat exchanger for cooling the cooling medium with a primary coolant. The heat exchanger may be a liquid-liquid heat exchanger for cooling with river water or sea water as primary coolant or an air cooler for cooling with air as primary coolant. The heat exchanger may also be a wet air cooler using evaporation of water into air for cooling the cooling medium.

In a preferred embodiment, the tube bundle reactor has vertically arranged reaction tubes and comprises at least one distributor arranged above the entry of the reaction tubes, having openings for supplying liquid to each of the reaction tubes. The distributor preferably comprises separate openings for separately supplying two liquids to each of the reaction tubes, in particular for separately supplying a propene feed stream and a hydrogen peroxide feed stream to each of the reaction tubes. Suitable distributors are known from the prior art, for example from WO 2005/025716. This embodiment of the reactor is suitable for operating the process of the invention with trickle flow of liquid in the catalyst fixed bed.

The tube bundle reactor may additionally comprise a phase separator arranged downstream of the end of the reaction tubes for separating liquid phases of a multi-phase reaction mixture exiting at the end of the reaction tubes. Suitable phase separators are known from the prior art, for example from WO 2008/141734.

The tube bundle reactor preferably comprises temperature sensors arranged in the center of reaction tubes. Preferably, from 1 to 50 temperature sensors are used. Temperature sensors may be arranged in one or more rows within a corresponding number of reaction tubes. However, it is preferred to use separate temperature sensors in a corresponding number of reaction tubes. Temperature sensors are preferably distributed within the tube bundle to monitor homogeneity of the temperature distribution within the tube bundle. Preferably, a set of temperature sensors is used within a reaction tube or in several reaction tubes at comparable locations within the tube bundle with the temperature sensors located at different distances along the length of the catalyst fixed bed, preferably at distances varying by 0.2 to 1.5 m, in order to monitor the temperature profile along the length of the catalyst fixed bed.

The reaction is carried out in the presence of a shaped titanium silicalite catalyst which is arranged as a fixed bed in the reaction tubes. The titanium silicalite preferably has a MFI or MEL crystal structure. Most preferably a titanium silicalite-1 with MFI structure as known from EP 0 100 119 A1, is used. The shaped titanium silicalite catalyst is preferably employed in the form of granules, extrudates or shaped bodies. Shaping can be carried out by any method known from the prior art for shaping a titanium silicalite powder. Preferably, the shaped titanium silicalite catalyst is prepared by an extrusion process where a kneadable mass of a titanium silicalite powder, a liquid, a binder or binder precursor, and optionally processing additives is pressed through a die, the formed strands are cut, dried to green bodies and calcined to form extrudates. The shaped titanium silicalite catalyst is therefore preferably in the form of extrudates, preferably having a cylindrical shape, where the edges at the end of the cylinders may optionally be rounded. The cylinders of such shaped catalyst preferably have a diameter of from 1 to 5 mm and a length of from 2 to 7 mm. The extrudates preferably comprise a silica binder. Suitable binder precursors for a silica binder that can be used in an extrusion process are fumed or precipitated silicas, silica sols, silicone resins or silicone oils, such as polydimethylsiloxanes, and tetraalkoxysilanes, such as tetraethoxysilane. Shaping can be carried out with a calcined titanium silicalite powder or with an uncalcined titanium silicalite powder still containing template molecules within the zeolite framework. When shaping is carried out with an uncalcined titanium silicalite powder, the catalyst is calcined after shaping in order to remove the template from the zeolite framework.

The catalyst fixed bed preferably extends over more than 70% of the length of the reaction tubes, more preferably over 90 to 98% of the length of the reaction tubes. In a preferred embodiment, a packing of inert material is arranged in the reaction tubes upstream of the catalyst fixed bed, preferably with a length of from 0.2 to 1.0 m. The inert material may be shaped in the same way or in a shape differing from the titanium silicalite catalyst. Preferred inert materials are glass beads. The packing of inert material provides an even distribution of flow and a mixing of liquid streams that are introduced separately into the reaction tubes before the mixture comprising propene and hydrogen peroxide enters the catalyst fixed bed.

The amount of catalyst employed and the rate at which the mixture comprising propene, hydrogen peroxide and methanol solvent is introduced into the reaction tubes are preferably chosen to provide a hydrogen peroxide conversion at full load of the reactor of more than 90%, preferably at least 95%, upon passage of the mixture through the reaction tubes.

The reaction is preferably carried out at a pressure of at least 1.9 MPa. The pressure is preferably from 1.9 to 5.0 MPa, more preferably 2.1 to 3.6 MPa and most preferably 2.4 to 2.8 MPa. Using an excess of propene at a high pressure provides high reaction rate and hydrogen peroxide conversion and at the same time high selectivity for propene oxide.

Preferably, a mixture comprising propene, hydrogen peroxide and methanol solvent is passed through the catalyst fixed bed in down flow mode, preferably with a superficial velocity from 1 to 100 m/h, more preferably 5 to 50 m/h, most preferred 5 to 30 m/h, at full load of the reactor. The superficial velocity is defined as the ratio of volume flow rate/cross section of the catalyst bed. Additionally it is preferred to pass the reaction mixture through the catalyst bed with a liquid hourly space velocity (LHSV) of from 1 to 20 $h^{-1}$, preferably 1.3 to 15 $h^{-1}$, at full load of the reactor. It is particularly preferred to arrange the parallel reaction tubes vertically and pass a mixture comprising propene, hydrogen peroxide and methanol solvent through the reaction tubes in down-flow in trickle mode. Suitable conditions for maintaining the trickle mode during the epoxidation reaction are disclosed in WO 02/085873 on page 8 line 23 to page 9 line 15. Preferably, two liquid feed streams are fed separately to the reaction tubes, a first liquid feed stream comprising hydrogen peroxide and methanol solvent and a second liquid feed stream comprising propene. Separate feeding of two liquid feed streams to the reaction tubes allows to achieve the same molar ratio of propene to hydrogen peroxide in each reaction tube at reaction conditions where the starting mixture of propene, hydrogen peroxide and methanol solvent is not completely miscible and may form two separate liquid phases.

Most preferably, the epoxidation reaction is carried out with the catalyst fixed bed maintained in a trickle mode at a pressure close to the vapor pressure of propene at the reaction temperature, using an excess of propene that provides a mixture comprising propene, hydrogen peroxide and methanol solvent, which mixture comprises two liquid phases, a first phase rich in propene and a second phase rich in methanol and hydrogen peroxide.

The reaction temperature is preferably from 20 to 80° C., more preferably from 25 to 60° C. Cooling medium is passed through the cooling jacket in order to remove the heat of reaction of the epoxidation reaction. The temperature and the amount of cooling medium and, if the cooling jacket has an additional withdrawal point for cooling medium, the fraction of cooling medium withdrawn at this additional withdrawal point are adjusted to provide an even temperature distribution along the length of the catalyst fixed bed within a reaction tube at full load of the reactor. Preferably, the temperature distribution along the length of the catalyst fixed bed is adjusted to keep the reaction temperature along 70 to 98%, preferably along 80 to 95%, of the length of the catalyst fixed bed within a range of less than 5° C., preferably within a range of from 0.5 to 3° C. at full load of the reactor. The temperature of the cooling medium fed to the feed point is preferably adjusted to a value 3 to 13° C. lower than the maximum temperature in the catalyst fixed bed at full load of the reactor. When cooling medium is withdrawn at an additional withdrawal point, the fraction of cooling medium withdrawn at the additional withdrawal point is preferably from 10 to 70%, more preferably from 30 to 55%. When the tube bundle reactor has several additional withdrawal points for cooling medium, cooling medium may be withdrawn at only one or at several additional withdrawal points at the same time and cooling medium may be withdrawn at different additional withdrawal points during the course of the reaction.

An essential part of the process of the invention are the operating conditions during start-up of the reaction with a fresh or a regenerated catalyst until full load of the reactor is reached.

During start-up of the reaction, cooling medium is fed to the cooling jacket at a constant rate for full load of the reactor. The entry temperature of the cooling medium is kept essentially constant at a value in the range of from 20° C. to 50° C., and the variation of the temperature of the cooling medium during start-up of the reaction is preferably less than 10° C., more preferably less than 7° C.

Methanol solvent is fed to the reaction tubes during start-up of the reaction at a feeding rate of from 50 to 100% of a feeding rate for full load of the reactor. The methanol feeding rate during start-up of the reaction is preferably in the range of from 60 to 100% of the feeding rate for full load of the reactor.

Hydrogen peroxide is fed to the reaction tubes during start-up of the reaction at a feeding rate that starts with no more than 10% of the feeding rate for full load of the reactor and is increased continuously or stepwise to the rate for full load of the reactor. The feeding rate for hydrogen peroxide is increased to maintain a maximum temperature in the fixed bed of no more than 60° C. and a temperature difference between the maximum temperature in the fixed bed and the cooling medium entry temperature of no more than 20° C. Preferably, the feeding rate for hydrogen peroxide is increased to maintain the difference between the maximum temperature in the fixed bed and the cooling medium entry temperature in the range of from 1 to 13° C. When the feeding rate for hydrogen peroxide is between 50% and 100% of the feeding rate for full load of the reactor, the difference between the maximum temperature in the fixed bed and the cooling medium entry temperature is preferably maintained in the range of from 4 to 13° C. When the feeding rate for hydrogen peroxide is increased stepwise, the steps are preferably no more than 20% of the feeding rate for full load of the reactor, more preferably no more than 10% of the feeding rate for full load of the reactor. Preferably, the increase in the feed rate of hydrogen peroxide is performed at a rate or in steps small enough to maintain a maximum temperature in the fixed bed of no more than 50° C.

Propene is fed to the reaction tubes during start-up of the reaction at a feeding rate of from 20 to 100% of the feeding rate for full load of the reactor. When the initial feed rate for propene is less than the feeding rate for full load of the reactor, the feeding rate for propene is increased when the molar ratio of propene to hydrogen peroxide reaches the molar ratio for full load of the reactor. The molar ratio of propene to hydrogen peroxide during start-up of the reaction will therefore be at least as high as for full load of the reactor and may be initially higher. The feeding rate for propene during start-up of the reaction is preferably at least 50% of the feeding rate for full load of the reactor in order to achieve high propene oxide selectivity and a shortened start-up phase.

The time period for start-up of the reaction from starting to feed hydrogen peroxide until reaching full load of the reactor is typically from 1 to 300 h, preferably from 2 to 140 h.

Increasing the feeding rate for hydrogen peroxide slow enough to keep the maximum temperature in the fixed bed at no more than 60° C. and the temperature difference between the maximum temperature in the fixed bed and the cooling medium entry temperature at no more than 20° C. prevents breakage of catalyst shaped bodies during start-up of the epoxidation reaction. Feeding methanol solvent at 50 to 100% of the rate for full load of the reactor and cooling medium at the rate for full load of the reactor during start-up of the epoxidation reaction allows to reach full load of the reactor in a shorter time compared to start-up of the epoxidation reaction at a lower solvent feed rate, as would be the case for starting up the epoxidation with the same proportions of propene, hydrogen peroxide and methanol solvent at reduced feed rates for all components.

In a preferred embodiment, ammonia is added to a feed stream to the reactor, preferably to the methanol solvent, in an amount of from 100 to 3000 ppm, preferably from 300 to 2000 ppm, at full load of the reactor, based on the weight of the hydrogen peroxide fed at full load of the reactor, in order to improve epoxide selectivity. Preferably, ammonia is fed at a fixed ratio of ammonia to hydrogen peroxide while operating the reaction at full load of the reactor. During start-up of the reaction, ammonia is preferably fed at a feeding rate of from 20 to 100% of the feeding rate for full load of the reactor. When the initial feed rate for ammonia is less than the feeding rate for full load of the reactor, the feeding rate for ammonia is increased when the ratio of ammonia to hydrogen peroxide reaches the ratio for full load of the reactor. The ratio of ammonia to hydrogen peroxide during start-up of the reaction is therefore preferably at least as high as for full load of the reactor and may be initially higher. The feeding rate for ammonia during start-up of the reaction is preferably at least 40% of the feeding rate for full load of the reactor in order to achieve high propene oxide selectivity. Adding ammonia to a feed stream during start-up of the reaction allows for a more rapid increase of the hydrogen peroxide feed rate and thus reduces the time period for start-up of the reaction from starting to feed hydrogen peroxide until reaching full load of the reactor. During start-up of the reaction, methanol solvent and ammonia are preferably fed to the reaction tubes for a period of from 15 min to 24 h before the feeding of hydrogen peroxide is started, in order to neutralize the acidity of the fresh or regenerated catalyst and achieve high propene oxide selectivity early on.

A fresh or a dry regenerated shaped titanium silicalite catalyst is preferably conditioned with methanol before start-up of the reaction. The catalyst may be conditioned by contacting it with methanol vapor or a gas stream comprising methanol vapor. Preferably, the catalyst is conditioned by contacting it with a first conditioning liquid comprising more than 60% by weight water and less than 40% by weight methanol to provide a conditioned catalyst and optionally further contacting it with at least one further conditioning liquid having a methanol content higher than the methanol content of the first conditioning liquid, where at least one of the conditioning liquids comprises water and from 25 to 45% by weight methanol. The combined amount of water and methanol in the conditioning liquids is preferably at least 95% by weight. The contacting with the one or more conditioning liquids is preferably carried out as described in international patent application PCT/EP2015/066814. Conditioning a dry shaped titanium silicalite as described above prevents breaking of the shaped catalyst upon contact with the liquid methanol solvent during start-up of the reaction.

The titanium silicalite catalyst will gradually lose catalytic activity during continuous epoxidation of propene with hydrogen peroxide at full load of the reactor. The temperature and the amount of cooling medium fed to the cooling jacket and, if an additional withdrawal point for cooling medium is used, the fraction of cooling medium withdrawn at the additional withdrawal point, are preferably adjusted to compensate for the decrease in catalyst activity. Preferably, the reaction temperature is increased in order to maintain sufficient conversion of hydrogen peroxide despite decreasing catalyst activity.

When, due to catalyst deactivation, the conversion of hydrogen peroxide falls below the desired level or the rise in reaction temperature necessary for maintaining the desired conversion of hydrogen peroxide leads to an undesired level of by-product formation, the continuous epoxidation is preferably interrupted to replace or regenerate the titanium silicalite catalyst. Preferably, the catalyst is regenerated within the reaction tubes. Regeneration within the reaction tubes can be achieved by methods known from the prior art, such as passing a gas stream at a temperature of from 200 to 600° C. through the catalyst fixed bed, passing a solvent stream through the catalyst bed or passing a solution of hydrogen peroxide through the catalyst bed in the absence of propene.

The titanium silicalite catalyst is preferably regenerated by passing a methanol solvent through the catalyst fixed bed at a temperature of from 100 to 200° C. for a period of 0.5 to 48 hours, more preferably 20 to 36 hours and most preferably 20 to 24 hours. The methanol solvent used for regenerating the catalyst preferably comprises more than 90% methanol and less than 10% water and more preferably more than 96 wt.-% methanol and less than 4% water. The methanol solvent is preferably a technical grade methanol, a solvent stream recovered in the work-up of the epoxidation reaction mixture or a mixture of both. The methanol solvent is preferably passed through the catalyst fixed bed in down flow mode and most preferably the flow rate is adjusted to maintain a trickle flow in the catalyst fixed bed. Regeneration may be performed at a constant temperature or using a temperature program. Passing the methanol solvent through the catalyst fixed bed is preferably started at the reaction temperature of the epoxidation reaction. The temperature is then raised to at least 100° C. and maintained at a temperature of at least 100° C. for the time necessary to carry out regeneration. Thereafter, the temperature is lowered back to the temperature used for epoxidation. Finally the methanol flow is stopped or the epoxidation is recommenced by starting to feed propene and hydrogen peroxide to the tube bundle reactor. In such a temperature program, raising and lowering of the temperature is preferably performed at a rate of from 5 to 30° C./h. During regeneration the pressure is adjusted to maintain the major part of the methanol solvent in the liquid state. The necessary pressure may be attained as the autogenous vapor pressure by evaporating part of the methanol solvent or by supplying an inert gas such as nitrogen. At least a part of the solvent that is passed through the catalyst fixed bed may be reused for regenerating the catalyst without prior purification. Preferably, the methanol solvent is passed through the catalyst fixed bed without reuse for a period of from 2% to 70% of the time used for regeneration and thereafter all the methanol solvent that is passed through the catalyst fixed bed is returned to the regeneration, creating a closed loop for washing the catalyst with a methanol solvent for the remainder of regeneration time. This reduces the amount of methanol needed for regenerating the catalyst.

After replacing or regenerating the titanium silicalite catalyst, the epoxidation reaction is recommenced, carrying out the start-up of the reaction as described above.

The propene oxide formed by the epoxidation of propene can be separated from the reaction mixture exiting the reaction tubes by any method known from the prior art.

Preferably, the reaction mixture is subjected to a pressure reduction and propene vapor formed by the pressure reduction is recompressed and cooled to recover propene by condensation. The compressed propene vapor is preferably fed to a propene distillation column and separated into an overhead product comprising non-reacted propene and a bottoms product containing compounds having a boiling point higher than propene, such as propene oxide and methanol solvent. The overhead product comprising non-reacted propene can be recycled to the epoxidation reaction. The bottoms product can be combined with the liquid mixture remaining after the pressure reduction. The liquid mixture remaining after the pressure reduction is preferably separated by distillation in a pre-separation column to provide an overhead product comprising propene oxide, methanol and residual propene and a bottoms product comprising methanol, water and non-reacted hydrogen peroxide. The pre-separation column is preferably operated to provide an overhead product comprising from 20 to 60% of the methanol contained in the liquid phase of the last pressure reduction step. The pre-separation column preferably has from 5 to 20 theoretical separation stages in the stripping section and less than 3 theoretical separation stages in a rectifying section and is most preferably operated without reflux and without a rectifying section to minimize the residence time of propene oxide in the pre-separation column. The pre-separation column is preferably operated at a pressure of from 0.16 to 0.3 MPa. Propene oxide and methanol are condensed from the overhead product of the pre-separation column and propene is preferably stripped from the resulting condensate in a propene stripping column which provides a bottom stream comprising propene oxide and methanol which is essentially free of propene.

Propene oxide is preferably separated from the bottoms stream of the propene stripping column in an extractive distillation using water as the extraction solvent. The extractive distillation is preferably operated with additional feeding of a reactive compound containing an unsubstituted $NH_2$ group and capable of reacting with acetaldehyde during the extractive distillation, as described in WO 2004/048335. Extractive distillation with a reactive compound provides a high purity propene oxide containing less than 50 ppm of carbonyl compounds.

Methanol can be recovered from the bottoms product of the pre-separation column by distillation. Preferably, the bottoms product of the pre-separation column is subjected to a catalytic hydrogenation with hydrogen to remove non-reacted hydrogen peroxide remaining from step a), as described in WO 03/093255, before methanol is separated by distillation. Such catalytic hydrogenation reduces the amount of carbonyl compounds and acetals in the methanol separated by distillation, which is advantageous when the methanol is recycled to the reaction of step a). The bottoms product of the extractive distillation is preferably combined with the bottoms product of the pre-separation column, preferably before subjecting it to hydrogenation, in order to recover methanol. When hydrazine is used as the reactive compound in the extractive distillation, passing the bottoms product of the extractive distillation to the catalytic hydrogenation will convert non-reacted hydrazine and hydrazones formed from carbonyl compounds to ammonia and amines. The recovered methanol can be recycled as solvent to the epoxidation reaction. Preferably, the recovered methanol or the bottoms product of the pre-separation column, optionally combined with bottoms product of the extractive distillation and preferably after a catalytic hydrogenation, is treated to remove organic nitrogen compounds as described in WO 2004/048354, more preferably by subjecting it to an acid treatment. Most preferably, the recovered methanol is passed over a cation exchanger in the hydrogen form before it is recycled to the epoxidation reaction. Removal of organic nitrogen compounds, in particular amines, avoids deactivation of the titanium silicalite catalyst upon recycling of methanol.

EXAMPLE

Feed rates suitable for the start-up of an epoxidation reaction, reacting propene with 70% by weight aqueous hydrogen peroxide in a methanol solvent at a weight ratio of 3.62:1:4.48 at full load of the reactor with addition of 1000 ppm ammonia, using a regenerated extruded titanium silicalite catalyst in a tube bundle reactor cooled with water of 25° C., and increasing the hydrogen peroxide feed stepwise in steps of 10% of the feeding rate for full load of the reactor, are given in table 1. Table 1 also gives the values for the temperature difference $\Delta T$ between the maximum temperature in the fixed bed and the cooling medium entry temperature and the time from starting the hydrogen peroxide feed that can be attained with this start-up procedure.

TABLE 1

| Feed rates in % of feed rates at full load of the reactor | | | | $\Delta T$ in ° C. | Time from starting hydrogen peroxide feed in h |
|---|---|---|---|---|---|
| Hydrogen peroxide | Methanol | Propene | Ammonia | | |
| 0 | 100 | 60 | 50 | 0 | |
| 10 | 100 | 60 | 50 | 1.0 | 0 |
| 20 | 100 | 60 | 50 | 1.9 | 1 |
| 30 | 100 | 60 | 50 | 2.0 | 1.25 |
| 40 | 100 | 60 | 50 | 3.6 | 1.5 |
| 50 | 100 | 60 | 50 | 4.9 | 1.75 |
| 60 | 100 | 60 | 60 | 5.3 | 2 |
| 70 | 100 | 70 | 70 | 7.8 | 3 |
| 80 | 100 | 80 | 80 | 8.6 | 4 |
| 90 | 100 | 90 | 90 | 9.6 | 8 |
| 100 | 100 | 100 | 100 | 11.3 | 25 |

The invention claimed is:
1. A process for the epoxidation of propene by continuously reacting propene with hydrogen peroxide in a methanol solvent and in the presence of a shaped titanium silicalite catalyst; wherein:
   a) the reaction is in a tube bundle reactor comprising a multitude of parallel reaction tubes and a cooling jacket enclosing the reaction tubes;
   b) the catalyst is arranged as a fixed bed in the reaction tubes;
   c) the molar ratio of propene to hydrogen peroxide is in the range of from 2.5:1 to 6:1 at full load of the reactor;
   d) during start-up of the reaction with a fresh or a regenerated catalyst until full load of the reactor is reached:
      i) cooling medium is fed to the cooling jacket at a constant rate for full load of the reactor, the entry temperature of the cooling medium being kept essentially constant at a value in the range of from 20° C. to 50° C.;
      ii) methanol solvent is fed to the reaction tubes at a feeding rate of from 50 to 100% of a feeding rate for full load of the reactor;
      iii) hydrogen peroxide is fed to the reaction tubes at a feeding rate that starts with no more than 10% of a feeding rate for full load of the reactor and is increased continuously or stepwise to the rate for full load of the reactor, increasing the feeding rate for hydrogen peroxide to maintain a maximum temperature in the fixed bed of no more than 60° C. and a temperature difference between the maximum temperature in the fixed bed and the cooling medium entry temperature of no more than 20° C.; and iv) propene is fed to the reaction tubes at a feeding rate of from 20 to 100% of a feeding rate for full load of the reactor, increasing the feeding rate for propene when the molar ratio of propene to hydrogen peroxide reaches the molar ratio for full load of the reactor.

2. The process of claim 1, wherein the parallel reaction tubes are arranged vertically and a mixture comprising propene, hydrogen peroxide and methanol solvent is passed through the reaction tubes in down-flow in trickle mode.

3. The process of claim 2, wherein a first liquid feed stream comprising hydrogen peroxide and methanol solvent and a second liquid feed stream comprising propene are fed separately to the reaction tubes.

4. The process of claim 1, wherein during start-up of the reaction the feeding rate for hydrogen peroxide is increased stepwise in steps of no more than 20% of the feeding rate for full load of the reactor.

5. The process of claim 4, wherein the parallel reaction tubes are arranged vertically and a mixture comprising propene, hydrogen peroxide and methanol solvent is passed through the reaction tubes in down-flow in trickle mode.

6. The process of claim 5, wherein a first liquid feed stream comprising hydrogen peroxide and methanol solvent and a second liquid feed stream comprising propene are fed separately to the reaction tubes.

7. The process of claim 4, wherein during start-up of the reaction the feeding rate for hydrogen peroxide is increased stepwise in steps of no more than 10% of the feeding rate for full load of the reactor.

8. The process of claim 1, wherein propene is used as a mixture with propane with a mass ratio of propane to the combined amounts of propane and propene of from 0.001 to 0.15.

9. The process of claim 8, wherein the parallel reaction tubes are arranged vertically and a mixture comprising propene, hydrogen peroxide and methanol solvent is passed through the reaction tubes in down-flow in trickle mode.

10. The process of claim 9, wherein a first liquid feed stream comprising hydrogen peroxide and methanol solvent and a second liquid feed stream comprising propene are fed separately to the reaction tubes.

11. The process of claim 8, wherein during start-up of the reaction the feeding rate for hydrogen peroxide is increased stepwise in steps of no more than 20% of the feeding rate for full load of the reactor.

12. The process of claim 8, wherein propene is used as a mixture with propane with a mass ratio of propane to the combined amounts of propane and propene of from 0.08 to 0.12.

13. The process of claim 12, wherein during start-up of the reaction the feeding rate for hydrogen peroxide is increased stepwise in steps of no more than 10% of the feeding rate for full load of the reactor.

14. The process of claim 1, wherein propene is reacted with hydrogen peroxide at a temperature of from 20 to 80° C. and a pressure of from 1.9 to 5.0 MPa.

15. The process of claim 14, wherein the parallel reaction tubes are arranged vertically and a mixture comprising propene, hydrogen peroxide and methanol solvent is passed through the reaction tubes in down-flow in trickle mode.

16. The process of claim 15, wherein a first liquid feed stream comprising hydrogen peroxide and methanol solvent and a second liquid feed stream comprising propene are fed separately to the reaction tubes.

17. The process of claim 14, wherein during start-up of the reaction the feeding rate for hydrogen peroxide is increased stepwise in steps of no more than 20% of the feeding rate for full load of the reactor.

18. The process of claim 14, wherein propene is used as a mixture with propane with a mass ratio of propane to the combined amounts of propane and propene of from 0.001 to 0.15.

19. The process of claim 14, wherein during start-up of the reaction the feeding rate for hydrogen peroxide is increased stepwise in steps of no more than 10% of the feeding rate for full load of the reactor.

20. The process of claim 19, wherein propene is used as a mixture with propane with a mass ratio of propane to the combined amounts of propane and propene of from 0.08 to 0.12.

* * * * *